(12) United States Patent
Fu et al.

(10) Patent No.: US 9,151,725 B2
(45) Date of Patent: Oct. 6, 2015

(54) HUMIDITY MEASUREMENT DEVICE AND METHOD

(75) Inventors: Jun Fu, Beijing (CN); Wei Chang, Beijing (CN); Lianbo Yu, Beijing (CN)

(73) Assignee: BEIJING POLYMER SENSING TECHNOLOGY CO., LTD., Beijing (CN)

( * ) Notice: Subject to any disclaimer, the term of this patent is extended or adjusted under 35 U.S.C. 154(b) by 617 days.

(21) Appl. No.: 13/518,028

(22) PCT Filed: Apr. 26, 2010

(86) PCT No.: PCT/CN2010/072195
§ 371 (c)(1), (2), (4) Date: Jun. 21, 2012

(87) PCT Pub. No.: WO2011/075971
PCT Pub. Date: Jun. 30, 2011

(65) Prior Publication Data
US 2012/0255354 A1    Oct. 11, 2012

(30) Foreign Application Priority Data
Dec. 23, 2009  (CN) .......................... 2009 1 0243831

(51) Int. Cl.
G01N 27/22    (2006.01)
(52) U.S. Cl.
CPC ............ *G01N 27/223* (2013.01); *G01N 27/228* (2013.01)
(58) Field of Classification Search
CPC .. G01N 27/223; G01N 27/227; G01N 27/228
USPC ...................................... 73/335.04
See application file for complete search history.

(56) References Cited

U.S. PATENT DOCUMENTS

| 4,816,748 A | * | 3/1989 | Tazawa et al. .............. 324/694 |
| 5,235,267 A | * | 8/1993 | Schoneberg et al. ........ 324/71.5 |

(Continued)

FOREIGN PATENT DOCUMENTS

| CN | 1455250 A | 11/2003 |
| CN | 2837787 Y | 11/2006 |

(Continued)

OTHER PUBLICATIONS

Gu Lei et al. A novel integrated humidity sensor compatible with CMOS. Micronanoelectric Technology, Jul.-Aug. 2003, No. 7/8, pp. 461-463.

*Primary Examiner* — Harshad R Patel
*Assistant Examiner* — Punam Roy
(74) *Attorney, Agent, or Firm* — Harness, Dickey & Pierce, P.L.C.

(57) ABSTRACT

A humidity measurement device comprises a capacitance measurement unit (101) and a microcontroller (102). The capacitance measurement unit (101) is used to output a frequency signal of a humidity-sensitive capacitor (C1) by the humidity-sensitive capacitor (C1) and a frequency signal of a reference capacitor (C2) by the reference capacitor (C2) respectively. The microcontroller (102) is used to obtain a frequency value of the humidity-sensitive capacitor (C1) and a frequency value of the reference capacitor (C2) based on the frequency signal of the humidity-sensitive capacitor (C1) and the frequency signal of the reference capacitor (C2), and obtain a current ambient humidity value by using a linear function relationship of a frequency difference between the humidity-sensitive capacitor (C1) and the reference capacitor (C2) and a humidity value. A humidity measurement method includes using the said humidity measurement device to measure a current ambient humidity value.

14 Claims, 6 Drawing Sheets

(56) References Cited

U.S. PATENT DOCUMENTS

| | | | |
|---|---|---|---|
| 5,402,075 A * | 3/1995 | Lu et al. | 324/664 |
| 5,677,476 A * | 10/1997 | McCarthy et al. | 73/29.01 |
| 5,844,138 A | 12/1998 | Cota | |
| 6,553,813 B2 * | 4/2003 | Rynhart et al. | 73/73 |
| 6,756,793 B2 * | 6/2004 | Hirono et al. | 324/690 |
| 6,842,018 B2 * | 1/2005 | McIntosh | 324/664 |
| 7,176,700 B2 * | 2/2007 | Itakura et al. | 324/689 |
| 7,571,637 B2 * | 8/2009 | Chen et al. | 73/73 |
| 2005/0174129 A1 * | 8/2005 | Haider | 324/664 |
| 2005/0218465 A1 | 10/2005 | Cummins | |
| 2006/0037404 A1 * | 2/2006 | Watanabe | 73/714 |
| 2007/0273394 A1 * | 11/2007 | Tanner et al. | 324/664 |
| 2008/0257037 A1 * | 10/2008 | Isogai et al. | 73/335.04 |

FOREIGN PATENT DOCUMENTS

| | | |
|---|---|---|
| CN | 101308110 A | 11/2008 |
| CN | 101738422 B | 9/2012 |
| DE | 4103433 A1 * | 2/1991 |
| WO | WO-2009016594 A2 | 2/2009 |

* cited by examiner

HUMIDITY MEASUREMENT DEVICE AND METHOD

This application is a National Stage application of international application PCT/CN2010/072195 filed on Apr. 26, 2010, which claimed priority to Chinese patent application No. 200910243831.0 filed on Dec. 23, 2009. Both the international application and the Chinese application are incorporated herein by reference in their entireties.

FIELD OF THE INVENTION

The present invention relates to the field of measuring instrument, and in particular to a device for humidity measurement and a method thereof.

BACKGROUND OF THE INVENTION

Nowadays, humidity measurement has become an essential tool in environmental monitoring for HVAC (heating, ventilation, and air conditioning), communications base stations, building security, etc.

Currently, commercially available electronic devices for humidity measurement used in environmental monitoring achieve the measurement, conversion and transmission of humidity by activating a humidity-sensitive element. Generally, the humidity-sensitive element may be capacitive, or resistive. In resistive humidity-sensitive elements, the effect of humidity is the change in the electrical resistance of a material. The electrical resistance can vary dramatically, and is in a logarithmic relationship with the humidity to be measured, causing inconvenience in measurement and conversion, and limited range of measurement. The measurement range for relative humidity is normally between 20% RH and 95% RH with an accuracy of about 5%. In capacitive humidity-sensitive elements, the effect of humidity is the change in the electrical capacitance of a material, which is in a substantially linear relationship with the humidity to be measured. The measurement range can be 0% RH to 100% RH, hence the full range, with an accuracy of about 1% to 3%. As a result, humidity-sensitive capacitors are generally used for industrial use, e.g., as humidity-sensitive elements, while humidity-sensitive resistors are generally used for commercial use, e.g., as hygrometers.

However, both types of humidity-sensitive elements have the problem of high-temperature drift, and may have reduced accuracy due to condensation or dust, or even break down or be damaged in severe conditions.

SUMMARY OF THE INVENTION

In view of this, according to an embodiment of the present invention, a device for humidity measurement and a method thereof are provided, which can improve the accuracy and stability in humidity measurement.

According to an embodiment of the present invention, a device for humidity measurement is provided, including:

a capacitance measuring unit, adapted to output a frequency signal corresponding to a humidity-sensitive capacitor and a frequency signal corresponding to a reference capacitor by the humidity-sensitive capacitor and the reference capacitor, respectively; and a microcontroller, adapted to obtain frequency values representing the capacitances of the humidity-sensitive capacitor and the reference capacitor based on the frequency signals corresponding to the humidity-sensitive capacitor and the reference capacitor, and obtain a current ambient humidity value based on a linear function between humidity and the difference between the frequency values representing the capacitances of the humidity-sensitive capacitor and the reference capacitor.

Preferably, the microcontroller is further adapted to:

determine whether the obtained current ambient humidity value reaches a preset ambient humidity threshold, and if so, trigger a humidity-sensitive capacitor heating unit and a thermistor measuring unit; and obtain a first saturated vapor pressure at a humidity-sensitive capacitor surface temperature and a second saturated vapor pressure at a current ambient temperature based on the humidity-sensitive capacitor surface temperature and the current ambient temperature returned by the thermistor measuring unit respectively, and obtain an actual ambient humidity value based on the product of a humidity-sensitive capacitor surface humidity value and the ratio of the first saturated vapor pressure to the second saturated vapor pressure;

and the device further includes:

the humidity-sensitive capacitor heating unit, adapted to heat the humidity-sensitive capacitor by a heating resistor, so as to form a positive difference between humidity-sensitive capacitor surface temperature and ambient temperature; and the thermistor measuring unit, adapted to output a first resistance signal representing the humidity-sensitive capacitor surface temperature by a first thermistor, and to output a second resistance signal representing the current ambient temperature by a second thermistor.

Preferably, the device further includes:

an output unit, adapted to receive a pulse-width modulation (PWM) signal representing an ambient humidity value outputted by the microcontroller, convert the PWM signal into a constant-current signal, and output the constant-current signal.

Preferably, the device further includes a waterproofing and ventilating housing, which encloses the humidity-sensitive capacitor, the first thermistor and the heating resistor.

Preferably, the device further includes a protection housing, which encloses the second thermistor.

Preferably, the device further includes a plastic protective housing, which encloses the waterproofing and ventilating housing and the thermistor protection housing.

According to an embodiment of the present invention, a method for humidity measurement is provided, including:

receiving, by a microcontroller, a frequency signal corresponding to a humidity-sensitive capacitor and a frequency signal corresponding to a reference capacitor outputted by the humidity-sensitive capacitor and the reference capacitor, respectively;

obtaining, by the microcontroller, frequency values representing the capacitances of the humidity-sensitive capacitor and the reference capacitor based on the frequency signals corresponding to the humidity-sensitive capacitor and the reference capacitor; and obtaining, by the microcontroller, a current ambient humidity value based on a linear function between humidity and the difference between the frequency values representing the capacitances of the humidity-sensitive capacitor and the reference capacitor.

Preferably, the method further includes:

determining, by the microcontroller, whether the obtained current ambient humidity value reaches a preset ambient humidity threshold, and if so, heating the humidity-sensitive capacitor by a heating resistor, so as to form a positive difference between humidity-sensitive capacitor surface temperature and ambient temperature;

obtaining, by the microcontroller, a humidity-sensitive capacitor surface temperature and a current ambient temperature, based on a first resistance signal representing the humidity-sensitive capacitor surface temperature outputted by a first thermistor and a second resistance signal representing the current ambient temperature outputted by a second thermistor;

obtaining, by the microcontroller, a first saturated vapor pressure at the humidity-sensitive capacitor surface temperature and a second saturated vapor pressure at the current ambient temperature, based on the humidity-sensitive capacitor surface temperature and the current ambient temperature, respectively; and obtaining, by the microcontroller, an actual ambient humidity value based on the product of a humidity-sensitive capacitor surface humidity value and the ratio of the first saturated vapor pressure to the second saturated vapor pressure.

Preferably, the method further includes:

converting a pulse-width modulation (PWM) signal representing an ambient humidity value outputted by the microcontroller into a constant-current signal, and outputting the constant-current signal.

Preferably, the method further includes:

arranging a waterproofing and ventilating housing which encloses the humidity-sensitive capacitor, the first thermistor and the heating resistor.

Preferably, the method further includes:

arranging a protection housing which encloses the second thermistor.

Preferably, the method further includes:

arranging a plastic protective housing which encloses the waterproofing and ventilating housing and the thermistor protection housing.

In comparison with the prior art, the technical solutions according to the present invention can realize humidity measurement with a single-chip architecture, that is, achieve the activation and measurement of the humidity-sensitive capacitor by a microcontroller with the help of a small number of resistors and capacitors. The simple architecture lowers the impact of external factors on humidity measurement to the minimum level; and the microcontroller carries out both temperature compensation and non-linear compensation of the measured value, which can improve the measurement accuracy to the greatest extent possible. Moreover, an additional follower capacitor is provided in the capacitance measuring circuit, and in calculation the difference between the capacitances of the two branches is used as a variable of the humidity function, thereby cancelling out system errors and improving the measurement accuracy.

The present invention provides a condensation prevention design by adding a constant-current-driven heating resistor underneath the electrodes of the humidity-sensitive capacitor, to cause temperature difference between the humidity-sensitive capacitor and the ambient environment and prevent condensation, so that continuous humidity measurement can be achieved during the heating process without compromising the function of the product. Meanwhile, capacitance drift of the humidity-sensitive capacitor is reduced, and the humidity-sensitive capacitor's lifetime is increased.

Furthermore, the exterior structure of the device for humidity measurement according to the present invention adopts a two-layered design including a waterproofing and ventilating housing and a plastic protective housing, which can block off dust and splash without affecting humidity measurement and increase the humidity-sensitive element's lifetime to the greatest extent possible.

BRIEF DESCRIPTION OF THE DRAWINGS

For a better understanding of the technical solutions according to the embodiments of the present invention, accompanying drawings used in the description of the embodiments or the prior art are briefly described below. As a matter of course, these drawings are only some embodiments of the present invention, and other drawings may be obtained by those skilled in the art according to these drawings without inventive effort.

DETAILED DESCRIPTION OF THE EMBODIMENTS

The technical solutions according to the embodiments of the present invention will be described hereinafter in conjunction with the accompanying drawings in the embodiments of the present invention. As a matter of course, the embodiments described are only some embodiments of the present invention. Any other embodiment made by those skilled in the art based on the embodiments herein without inventive effort shall fall within the scope of protection of the present invention.

Figure 1:
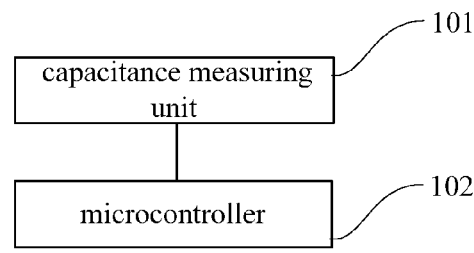
FIG. 1 is a structural diagram illustrating a device for humidity measurement according to an embodiment of the present invention.

As shown in FIG. 1, according to the present invention, a device for humidity measurement may include:

a capacitance measuring unit 101, adapted to output a frequency signal corresponding to a humidity-sensitive capacitor and a frequency signal corresponding to a reference capacitor by the humidity-sensitive capacitor and the reference capacitor, respectively; and a microcontroller 102, adapted to obtain frequency values representing the capacitances of the humidity-sensitive capacitor and the reference capacitor based on the frequency signals corresponding to the humidity-sensitive capacitor and the reference capacitor, and obtain a current ambient humidity value based on a linear function between humidity and the difference between the frequency values representing the capacitances of the humidity-sensitive capacitor and the reference capacitor.

According to the present invention, an additional follower capacitor is provided in the capacitance measuring circuit, and in calculation the difference between the capacitances of the two branches is used as a variable of the humidity function, thereby reducing system errors such as the temperature coefficient and voltage variations, reducing errors resulting from output oscillation, and hence improving the measurement accuracy.

Furthermore, humidity-sensitive capacitors are subject to condensation in high-humidity conditions, which may lead to capacitance drift, and reduced capacitor lifetime and measurement accuracy. Currently, the conventional design uses an additional heating component close to the humidity-sensitive capacitor, to heat the humidity-sensitive capacitor regularly. This condensation removing design uses a compulsorily executed process to interrupt the measuring function of the humidity-sensitive capacitor, and compulsorily heat the humidity-sensitive capacitor. It can be seen that this design cannot improve the measurement accuracy by preventing capacitance drift, and what is worse, it stops humidity measurement during heating, which compromises the function of the humidity measurement product.

To avoid common condensation effects in existing humidity measurement devices, the humidity measurement device according to the present invention heats the humidity-sensitive capacitor in a non-interrupting manner, which includes executing a dedicated approach when a condensation prevention function is on, so that humidity measurement is ensured without affecting the measurement accuracy while the humidity-sensitive capacitor is heated.

Figure 2:
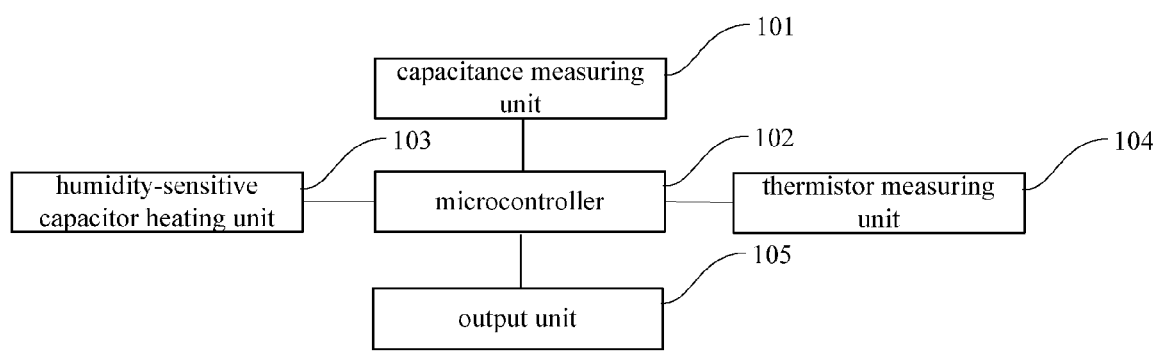
FIG. 2 is a structural diagram illustrating another device for humidity measurement according to an embodiment of the present invention.

To realize the condensation prevention function of the humidity measurement device, as shown in FIG. 2, the microcontroller 102 may be further adapted to:

determine whether the obtained current ambient humidity value reaches a preset ambient humidity threshold, and if so, trigger a humidity-sensitive capacitor heating unit 103 and a thermistor measuring unit 104; and obtain a first saturated vapor pressure at a humidity-sensitive capacitor surface temperature and a second saturated vapor pressure at a current ambient temperature based on the humidity-sensitive capacitor surface temperature and the current ambient temperature returned by the thermistor measuring unit 104 respectively, and obtain an actual ambient humidity value based on the product of a humidity-sensitive capacitor surface humidity value and the ratio of the first saturated vapor pressure to the second saturated vapor pressure.

And the device may further include:

the humidity-sensitive capacitor heating unit 103, adapted to heat the humidity-sensitive capacitor by a heating resistor, so as to form a positive difference between humidity-sensitive capacitor surface temperature and ambient temperature; and the thermistor measuring unit 104, adapted to output a first resistance signal representing the humidity-sensitive capacitor surface temperature by a first thermistor, and to output a second resistance signal representing the current ambient temperature by a second thermistor.

In the humidity measurement device, when ambient humidity reaches the heating protection threshold, the microcontroller triggers the heating of the humidity-sensitive capacitor, so as to form a positive difference between humidity-sensitive capacitor surface temperature and ambient temperature and prevent condensation. Moreover, two temperature measuring branches are designed in the humidity measurement device, for the humidity-sensitive capacitor surface temperature and the ambient temperature, respectively. The microcontroller, based on a correspondence relationship between the obtained temperatures and saturated vapor pressures, and in conjunction with the humidity on the humidity-sensitive capacitor, calculates the actual ambient humidity value, thus achieving accurate measurement of ambient humidity while providing heating protection.

To output the ambient humidity value obtained by the microcontroller, generally, the humidity measurement device may further include:

an output unit 105, adapted to receive a PWM signal representing an ambient humidity value outputted by the microcontroller 102, convert the PWM signal into a constant-current signal, and output the constant-current signal.

Generally, the microcontroller outputs a modulated PWM signal according to a calculated humidity value, and the PWM signal is converted into a constant-current signal by integral filtering.

The present invention will be described in more detail in conjunction with the embodiments of the present invention.

First Embodiment

Figure 3:
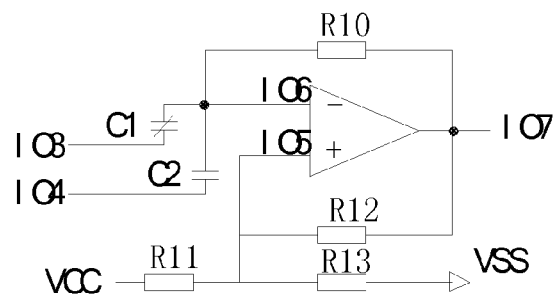
FIG. 3 is a circuit diagram illustrating an implementation of a capacitance measuring unit according to an embodiment of the present invention.

According to the embodiment of the present invention, an implementation of the capacitance measuring unit is provided. As shown in FIG. 3, the implementation mainly includes the following.

A capacitor and external resistors and capacitors form a Schmitt trigger, where the capacitors C1 and C2 are charged/discharged through R10. Specifically, C1 is the humidity-sensitive capacitor for measuring ambient temperature; C2 is the reference capacitor for compensating the humidity value measured by C1; and R11, R12 and R13 determine a high threshold V1 and a low threshold V2 at different times. When R12 and R13 are connected in parallel with each other, then both in series to R11, the low threshold V2 is determined. The operating principle of this circuit is described below.

Figure 4:
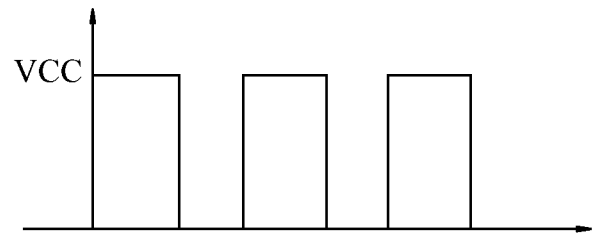
FIG. 4 is a waveform graph illustrating the output of an output terminal of a comparator in the implementation shown in FIG. 3.
Figure 5:
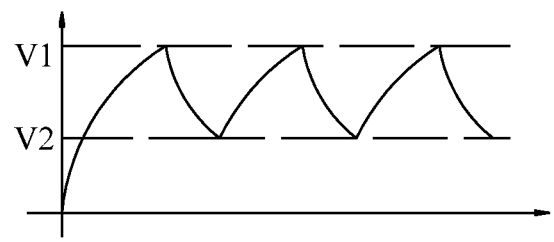
FIG. 5 is a waveform graph illustrating the output of an inverting terminal of a comparator in the implementation shown in FIG. 3.

To measure the humidity-sensitive capacitor C1, a pin IO4 of the microcontroller that is connected to C2 is set at high-impedance, a pin IO3 that is connected to C1 is grounded, and another pin is connected to the inverting terminal (−) of the comparator. At this point, the output of the comparator is VCC, which charges C1 through R10. R12 and R11 are connected in parallel with each other, then both in series to R13, thus determining the high threshold V1 for the non-inverting terminal (+) of the comparator. Once C1 is charged to V1, the output of the comparator switches to VSS. Then the humidity-sensitive capacitor C1 is discharged through R10. R12 and R13 are connected in parallel with each other, then both in series to R11, thus determining the low threshold V2 for the non-inverting terminal (+) of the comparator. Once C1 is discharged to V2, the output of the comparator switches to VCC, which continues to charge C1. The cycle repeats, and a square wave is formed at the output terminal of the comparator, as shown in FIG. 4. The waveform at the inverting terminal (−) of the comparator is shown in FIG. 5. When the capacitance of C1 varies with the humidity, the frequency of the square wave outputted at the output terminal of the comparator varies accordingly; hence the microcontroller can calculate the capacitance of C1 by measuring the frequency of the square wave, which can then be translated into the surface humidity value of C1.

An additional reference capacitor C2 is provided in the capacitance measuring unit. To measure C2, the pin IO3 of the microcontroller that is connected to C1 is set at high-impedance, the pin IO4 that is connected to C2 is grounded, and another pin is connected to the inverting terminal (−) of the comparator. The following process is similar to the case where C1 is to be measured, so details will be omitted here.

With the additional reference capacitor C2, the difference between oscillation frequencies corresponding to the capacitors C1 and C2 can be used as a variable of the humidity function, and the frequency difference has a linear relationship with the humidity.

Assuming the frequency measured by the capacitance measuring circuit for the humidity-sensitive capacitor C1 is Fs and the frequency measured for the reference capacitor C2 is F0, the humidity measurement function is:

$$RH=K\times(Fs-F0)+A$$

where RH denotes an ambient humidity value (% RH), K denotes the sensitivity of the humidity measurement circuit, and A denotes the intercept of the humidity measurement circuit.

K and A may be derived from two sets of frequencies corresponding to the humidity-sensitive capacitor and the reference capacitor measured in two standard humidity conditions, i.e., a humidity-sensitive capacitor frequency Fs1 and a reference capacitor frequency F01 measured at a humidity RH1, and a humidity-sensitive capacitor frequency Fs2 and a reference capacitor frequency F02 measured at a humidity RH2. Then K and A are given by:

$$K=(RH2-RH1)/(Fs2-F02-Fs1+F01)$$

$$A=(RH1\times(Fs2-F02)-RH2\times(Fs1-F01))/(Fs2-F02-Fs1+F01)$$

Through the non-linear compensation of the calculated humidity value according to the measured characteristics of the humidity-sensitive capacitor C1, system errors such as the temperature coefficient and voltage variations are reduced, as well as the errors resulting from output oscillation; hence the measurement accuracy is improved, and high measurement accuracy is ensured for the entire measurement range.

Second Embodiment

Figure 6:
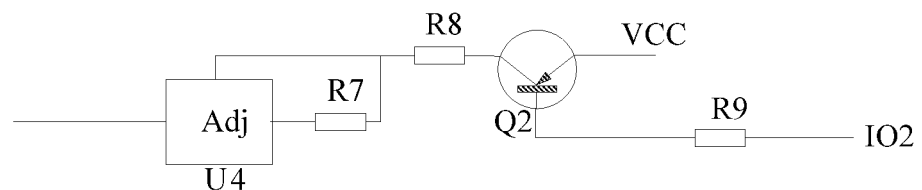
FIG. 6 is a circuit diagram illustrating an implementation of a humidity-sensitive capacitor heating unit according to an embodiment of the present invention.

According to the embodiment of the present invention, an implementation of the humidity-sensitive capacitor heating unit is provided. As shown in FIG. 6, the function of heating the humidity-sensitive capacitor to prevent it from condensation in a high-humidity condition is realized, where a resistor R8 functions as the heating resistor.

When the ambient humidity measured by the microcontroller reaches a heating protection threshold, the microcontroller sets a pin IO2 (of the microcontroller) at low-level. At this point, a Bipolar junction transistor (BJT) Q2 is turned on, causing a constant current Ih to flow through a Vcc pin, the heating resistor R8, a resistor R7, a negative output voltage regulator U4 and then a RH terminal. The condensation prevention function for the humidity-sensitive capacitor is on, the humidity-sensitive capacitor is heated up, and a positive difference between humidity-sensitive capacitor surface temperature and ambient temperature is formed, thereby preventing condensation. When the humidity is lower than the condensation prevention threshold, the pin IO2 is set at high-level, the PNP BJT Q2 is turned off, and the condensation prevention function for the humidity-sensitive capacitor is off.

While the humidity-sensitive capacitor is being heated, the microcontroller reduces its output current by subtracting from the current transmitted before the heating, so that the actual output current is maintained, and the humidity output of the product is not affected when heating protection is on, thereby achieving continuous humidity measurement. For example, assuming the voltage across the resistor R7 is a constant voltage of 1.25V and the heating current is 1.25/R7, the microcontroller subtracts the heating current from the output current so that the total output current remains the same; hence the current through the heating resistor does not affect the total output current and hence the continuous humidity measurement.

The conventional condensation removing design uses a compulsorily executed process to interrupt the measuring function of the humidity-sensitive capacitor, and compulsorily heat the humidity-sensitive capacitor. The design according to the present invention achieves uninterrupted measurement, that is, humidity measurement is not affected when the condensation prevention function is on.

Third Embodiment

Figure 7:
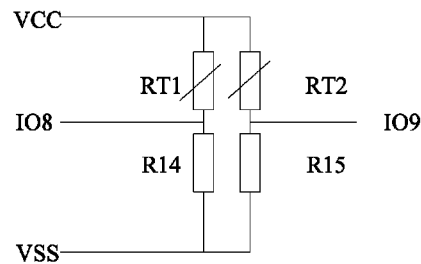
FIG. 7 is a circuit diagram illustrating an implementation of a thermistor measuring unit according to an embodiment of the present invention.

Corresponding to the implementation of the humidity-sensitive capacitor heating unit in the second embodiment, an implementation of the thermistor measuring unit is provided according to the embodiment of the present invention. As shown in FIG. 7, in cooperation with the humidity-sensitive capacitor heating unit, the thermistor measuring unit ensures normal operation of humidity measurement in high-humidity conditions.

As shown in FIG. 7, the microcontroller has a 12-bit Analog-to-Digital Converter (ADC) at a pin IO8, and a thermistor RT1 and a resistor R14 whose resistance is known are connected in series to form a voltage divider. When the resistance of RT1 is obtained, the temperature of RT1 can be calculated from it. The microcontroller also has a 12-bit ADC at a pin IO9, and a thermistor RT2 and a resistor R15 whose resistance is known are connected in series to form a voltage divider. When the resistance of RT2 is obtained, the temperature of RT2 can be calculated from it.

Two temperature measuring branches are provided in the present invention, in which RT1 is used for measuring the humidity-sensitive capacitor surface temperature and RT2 is used for measuring the ambient temperature. According to the two measured temperatures and the humidity on the humidity-sensitive capacitor, based on a built-in saturated vapor pressure table as shown in Table 1, the microcontroller may calculate the actual ambient humidity value, thus achieving accurate measurement of ambient humidity while providing heating protection.

TABLE 1

| Saturated vapor pressure table | |
|---|---|
| Temperature (degree Celsius) | Saturated vapor pressure (Pa) |
| 0 | 611.2 |
| 4 | 812.9 |
| 8 | 1071.4 |
| 12 | 1400.0 |
| 16 | 1814.2 |
| 20 | 2332.6 |
| 24 | 2976.6 |

TABLE 1-continued

Saturated vapor pressure table

| Temperature (degree Celsius) | Saturated vapor pressure (Pa) |
|---|---|
| 28 | 3771.1 |
| 32 | 4745.0 |
| 36 | 5931.3 |
| 40 | 7367.5 |
| 44 | 9096.3 |
| 48 | 11165.9 |
| 52 | 13630.4 |
| 56 | 16550.4 |
| 60 | 19993.3 |
| 64 | 24033.7 |
| 68 | 28754.3 |
| 72 | 34245.8 |
| 76 | 40607.7 |
| 80 | 47948.9 |

Specifically, an approach for calculating the actual ambient humidity value is described below.

When the measured humidity-sensitive capacitor surface humidity is RH0, the humidity-sensitive capacitor surface temperature is t1 and the ambient temperature is t2, the saturated vapor pressure at the temperature t1 and the saturated vapor pressure at the temperature t2 are obtained from the table, which are e1 and e2, respectively. Then the actual ambient humidity value is RH'=RH0×e1/e2.

Fourth Embodiment

Figure 8:
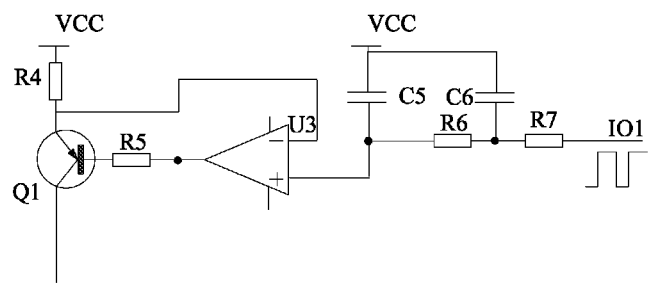
FIG. 8 is a circuit diagram illustrating an implementation of an output unit according to an embodiment of the present invention.

To output the ambient humidity value obtained by the microcontroller, the embodiment of the present invention provides an implementation of the output unit, as shown in FIG. 8.

In FIG. 8, IO1 denotes a pin of the microcontroller, and the microcontroller outputs a PWM signal at this pin. This implementation includes: a two-stage integral filtering circuit and a constant-current output circuit. Specifically, a resistor R7 and a capacitor C6 form the first stage of the integral filtering circuit, and a resistor R6 and a capacitor C5 form the second stage of the integral filtering circuit. The microcontroller outputs a modulated PWM signal according to a calculated humidity. The PWM signal is converted into a DC voltage signal V3 through the two stages of integral filtering, which is transmitted by an emitter follower U3 to the emitter of a BJT Q1 and thereby causes a constant current I at a resistor R4. At this point, I=(Vcc−V3)/R4, which is the final output current by the humidity measurement device. The final output current may be translated into a humidity value, and then provided to an operator.

Fifth Embodiment

Figure 9:
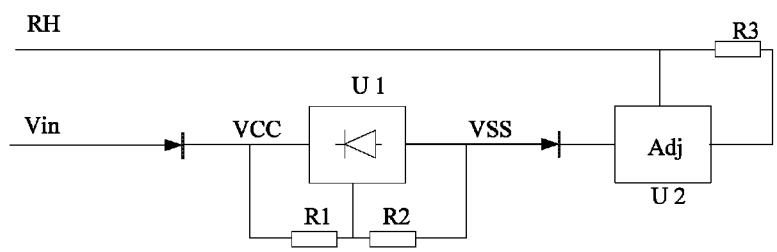
FIG. 9 is a circuit diagram illustrating a basic current and voltage regulating circuit according to an embodiment of the present invention.

Correspondingly, the embodiment provides a basic current and voltage regulating circuit as shown in FIG. 9, for providing a stable operating current for various circuits included in the humidity measurement device.

As shown in FIG. 9, a current flows through an adjustable precision shunt voltage regulator U1 to generate the system operating voltage Vcc (e.g., 3V). An adjustable 3-terminal positive voltage regulator U2 generates the system basic current (e.g., 4 mA), so that the currents in the circuits satisfies at least the basic current, thus ensuring the operation of the system.

It is noted that the implementations described with the embodiments above are for illustrative purposes only. As a matter of course, those skilled in the art may make modifications to the implementations in specific situations or to realize specific functions. The present invention is not limited to specific implementations.

Sixth Embodiment

When used in harsh conditions such as where there are a large amount of contamination particles in the air, the humidity measurement device has to meet the requirements of dust isolation and waterproofing. To this end, the embodiment of the present invention provides a humidity measurement device with the following protection measures, as shown in FIG. 10.

Figure 10:
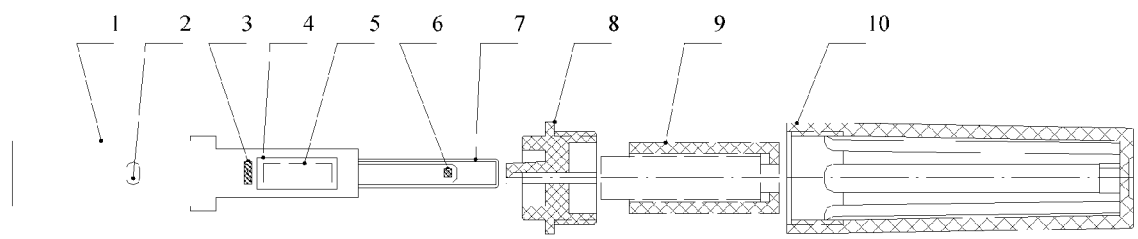
FIG. 10 is an exploded view illustrating the structure of a device for humidity measurement with a protection measure according to an embodiment of the present invention.

FIG. 10 illustrates a protection structure for humidity-sensitive capacitance measurement, including a PCB (1) and the following components arranged on the PCB (1): a mounting hole for connectors (2), a thermistor RT1(3), a humidity-sensitive capacitor (4), a heating resistor (5), a thermistor RT2 (6), a thermistor RT2 protection housing (7), a plastic connector (8), a waterproofing and ventilating housing (9) and a plastic protective housing (10). Specifically, the thermistor RT1(3), the heating resistor (5) and the humidity-sensitive capacitor (4) are enclosed inside the waterproofing and ventilating housing (9), while the thermistor RT2(6) is arranged outside the waterproofing and ventilating housing (9); hence, the thermistor RT1 (3) can be used to measure the surface temperature of the humidity-sensitive capacitor (4), while the thermistor RT2 (6) can be used to measure the ambient temperature. To make sure that the thermistor RT2 outside the waterproofing and ventilating housing will not be affected by dust and humidity in the environment, a protection housing may be provided outside the thermistor RT2, enclosing the thermistor RT2 inside the protection housing.

Figure 11:
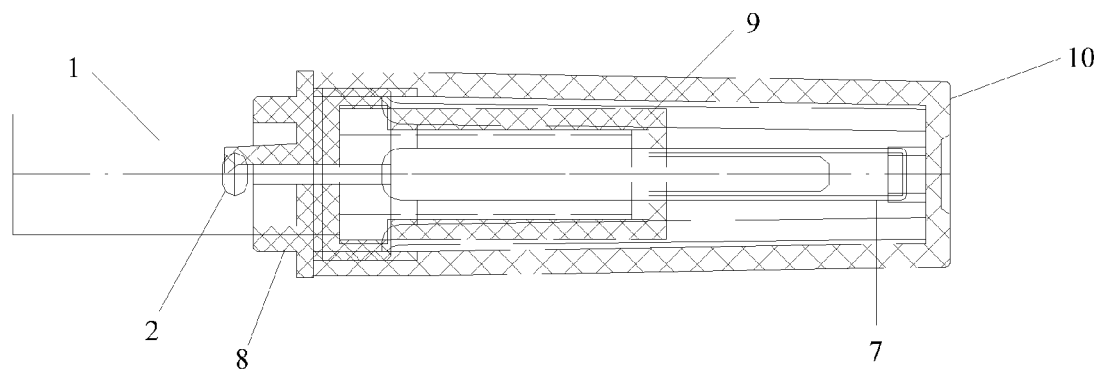
FIG. 11 is an assembled view illustrating the structure of a device for humidity measurement with a protection measure according to an embodiment of the present invention.

In addition, a plastic protective housing (10) may also be provided for enclosing the waterproofing and ventilating housing (9), the thermistor RT2(6) and the thermistor RT2 protection housing (7). FIG. 11 illustrates the relationship of assembly. The plastic protective housing (10) may be provided with openings as wide as permitted, to facilitate air exchange and thereby reduce the response time of humidity measurement.

To provide better sealing performance, an insulating sealant may be applied to where the plastic connector (8) is connected with the waterproofing and ventilating housing (9).

According to the embodiment, the exterior structure of the humidity measurement device adopts a two-layered design of the waterproofing and ventilating housing and the plastic protective housing, which can block off dust and splash without affecting humidity measurement and increase the humidity-sensitive element's lifetime to the greatest extent possible.

In addition, because of good sealing performance, the outer enclosing of the humidity measurement device can be cleaned with water to remove dust after being used in a harsh condition over a long period of time.

Seventh Embodiment

Figure 12:
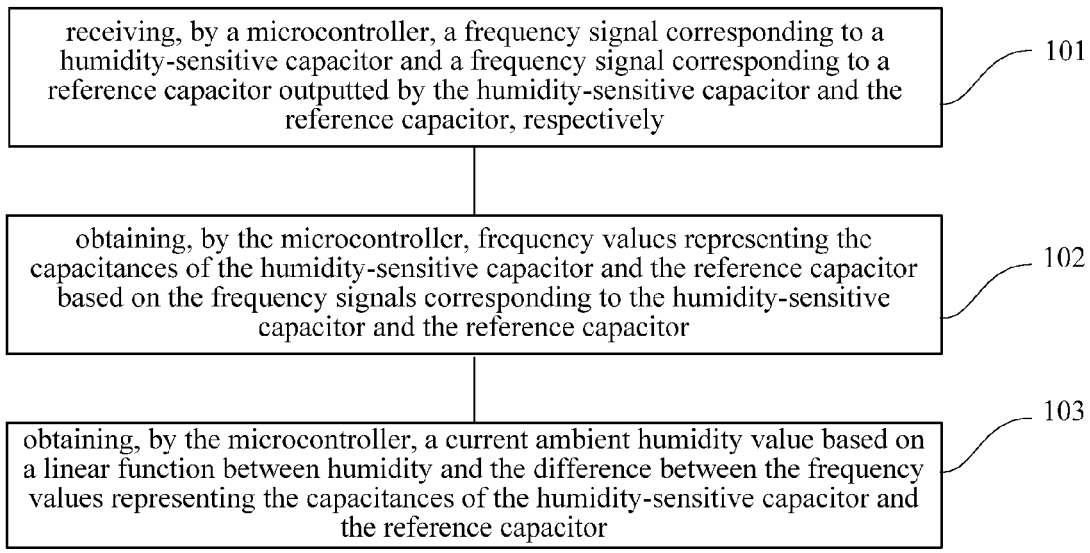
FIG. 12 is a flow chart of a method for humidity measurement according to an embodiment of the present invention.

Corresponding to the humidity measurement device described above, the embodiment of the present invention provides a humidity measurement method. FIG. 12 is a flow chart of the method, which mainly includes the following steps:

step 101, receiving, by a microcontroller, a frequency signal corresponding to a humidity-sensitive capacitor and a frequency signal corresponding to a reference capacitor outputted by the humidity-sensitive capacitor and the reference capacitor, respectively;

step 102, obtaining, by the microcontroller, frequency values representing the capacitances of the humidity-sensitive capacitor and the reference capacitor based on the frequency signals corresponding to the humidity-sensitive capacitor and the reference capacitor; and step 103, obtaining, by the microcontroller, a current ambient humidity value based on a linear function between humidity and the difference between the frequency values representing the capacitances of the humidity-sensitive capacitor and the reference capacitor.

According to the present invention, an additional follower capacitor (i.e., reference capacitor) is provided in the capacitance measuring circuit, and in calculation the difference between the capacitances of the two branches is used as a variable of the humidity function, thereby reducing system errors such as the temperature coefficient and voltage variations, reducing errors resulting from output oscillation, and hence improving the measurement accuracy.

Eighth Embodiment

Figure 13:
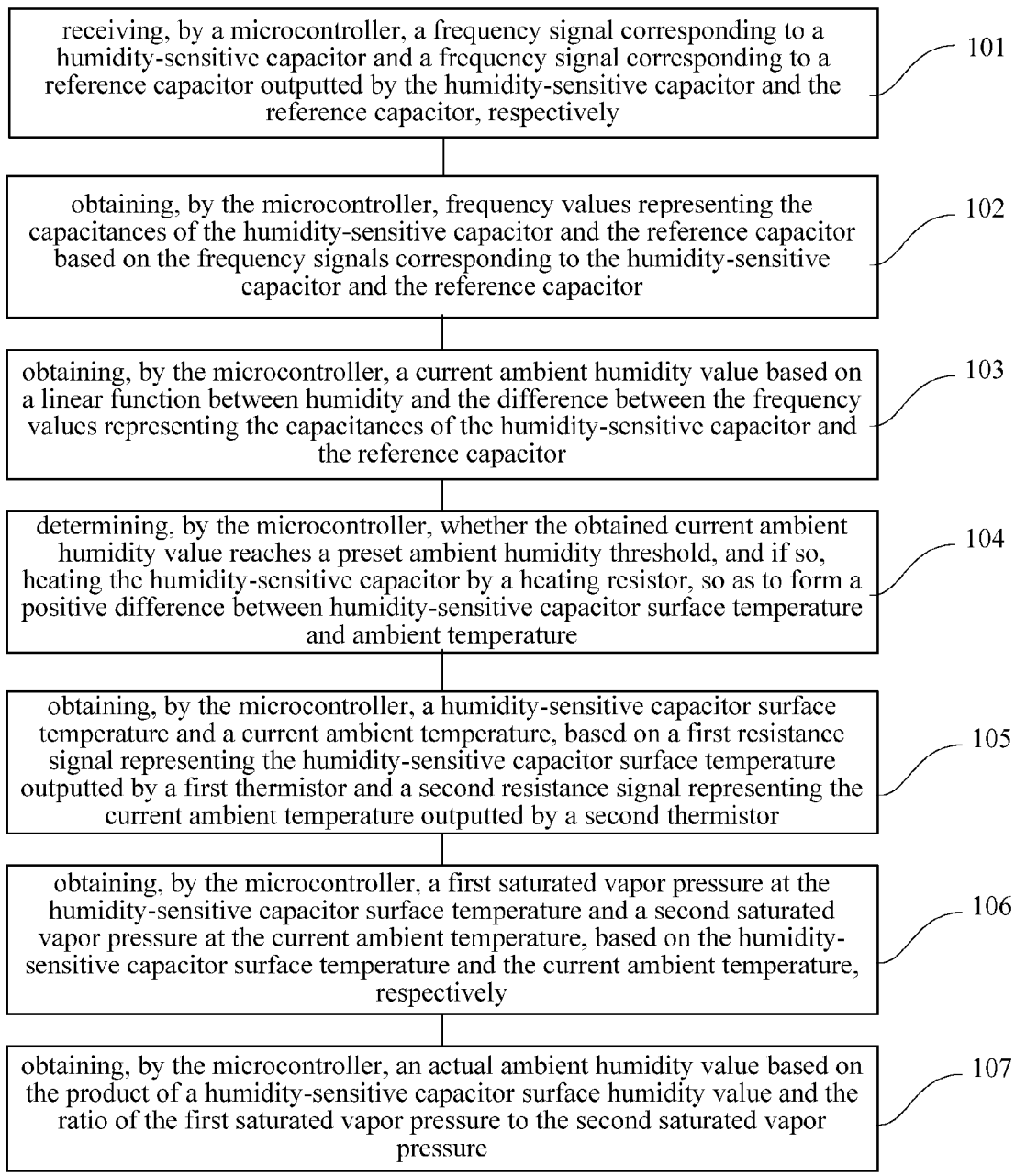
FIG. 13 is a flow chart of another method for humidity measurement according to an embodiment of the present invention.

In comparison with the seventh embodiment, this embodiment includes the following additional steps, as shown in FIG. 13:

step 104, determining, by the microcontroller, whether the obtained current ambient humidity value reaches a preset ambient humidity threshold, and if so, heating the humidity-sensitive capacitor by a heating resistor, so as to form a positive difference between humidity-sensitive capacitor surface temperature and ambient temperature;

step 105, obtaining, by the microcontroller, a humidity-sensitive capacitor surface temperature and a current ambient temperature, based on a first resistance signal representing the humidity-sensitive capacitor surface temperature outputted by a first thermistor and a second resistance signal representing the current ambient temperature outputted by a second thermistor;

step 106, obtaining, by the microcontroller, a first saturated vapor pressure at the humidity-sensitive capacitor surface temperature and a second saturated vapor pressure at the current ambient temperature, based on the humidity-sensitive capacitor surface temperature and the current ambient temperature, respectively; and step 107, obtaining, by the microcontroller, an actual ambient humidity value based on the product of a humidity-sensitive capacitor surface humidity value and the ratio of the first saturated vapor pressure to the second saturated vapor pressure.

Since humidity-sensitive capacitors are subject to condensation in high-humidity conditions, an additional heating resistor close to the humidity-sensitive capacitor is used to heat the humidity-sensitive capacitor, so that the humidity-sensitive capacitor surface temperature increases, and condensation is prevented. Moreover, humidity measurement is ensured without affecting the measurement accuracy while the humidity-sensitive capacitor is heated.

Generally, the microcontroller outputs a modulated PWM signal according to a calculated humidity value, and the PWM signal is converted into a constant-current signal by integral filtering.

To ensure normal operation of the humidity measurement device in harsh conditions, according to the embodiment, the humidity measurement device is designed to meet the requirements of dust isolation and waterproofing, specifically, by:

arranging a waterproofing and ventilating housing which encloses the humidity-sensitive capacitor, the first thermistor and the heating resistor; arranging a protection housing which encloses the second thermistor; and arranging a plastic protective housing which encloses the waterproofing and ventilating housing and the thermistor protection housing.

The exterior structure of the device for humidity measurement according to the present invention adopts a two-layered design including a waterproofing and ventilating housing and a plastic protective housing, which can block off dust and splash without affecting humidity measurement and increase the humidity-sensitive element's lifetime to the greatest extent possible.

In addition, because of good sealing performance, the outer enclosing of the humidity measurement device can be cleaned with water to remove dust after being used in a harsh condition over a long period of time.

The method embodiments are described in a relatively brief manner, due to their correspondence with the device embodiments. Details of those relating parts can be found in corresponding descriptions in device embodiments. The device embodiments described above are for illustrative purposes only. Units described as separate components are not necessarily physically separated. A component described as a unit is not necessarily a physical unit, i.e., it may be located in one place, or may as well be distributed in multiple network units. The object of an embodiment can be realized with some or all of the modules according to actual needs. Those skilled in the art will understand and implement without inventive effort.

Those skilled in the art will understand that all or some of the steps in the method embodiments above may be implemented with a computer program instructing related hardware. The program can be stored on a computer-readable storage medium, and when the program is executed, the process of a method embodiment above is performed. The storage medium includes magnetic disk, optical disc, read-only memory (ROM), random access memory (RAM), etc.

The description above of the embodiments enables those skilled in the art to implement or use the present invention. Various modifications to the embodiments will become apparent to those skilled in the art, and the general principle defined herein can be implemented in other embodiments without deviation from the scope of the present invention. Therefore, the present invention is not limited to the embodiments disclosed herein, but has the widest scope in accordance with the principle and novel characteristics disclosed herein.

The invention claimed is:

1. A device for humidity measurement, comprising:
a capacitance measuring unit, adapted to output a frequency signal corresponding to a humidity-sensitive capacitor and a frequency signal corresponding to a reference capacitor by the humidity-sensitive capacitor and the reference capacitor, respectively; and
a microcontroller, adapted to obtain frequency values representing the capacitances of the humidity-sensitive capacitor and the reference capacitor based on the frequency signals corresponding to the humidity-sensitive capacitor and the reference capacitor, and obtain a current ambient humidity value based on a function of $RH = K \times (Fs - F0) + A$, wherein RH denotes the current ambient humidity value, K denotes a sensitivity of the device for humidity measurement, and A denotes an intercept of the device for humidity measurement.

2. The device for humidity measurement according to claim 1, wherein the microcontroller is further adapted to:
determine whether the obtained current ambient humidity value reaches a preset ambient humidity threshold, and if so, trigger a humidity-sensitive capacitor heating unit and a thermistor measuring unit; and obtain a first saturated vapor pressure at a humidity-sensitive capacitor surface temperature and a second saturated vapor pressure at a current ambient temperature based on the humidity-sensitive capacitor surface temperature and the current ambient temperature returned by the thermistor measuring unit respectively, and obtain an actual ambient humidity value based on a product of a humidity-sensitive capacitor surface humidity value and a ratio of the first saturated vapor pressure to the second saturated vapor pressure;

and wherein the device further comprises:

the humidity-sensitive capacitor heating unit, adapted to heat the humidity-sensitive capacitor by a heating resistor, so as to form a positive difference between humidity-sensitive capacitor surface temperature and ambient temperature; and the thermistor measuring unit, adapted to output a first resistance signal representing the humidity-sensitive capacitor surface temperature by a first thermistor, and to output a second resistance signal representing the current ambient temperature by a second thermistor.

3. The device for humidity measurement according to claim 2, wherein the device further comprises a waterproofing and ventilating housing, which encloses the humidity-sensitive capacitor, the first thermistor and the heating resistor.

4. The device for humidity measurement according to claim 3, wherein the device further comprises a protection housing, which encloses the second thermistor.

5. The device for humidity measurement according to claim 4, wherein the device further comprises a plastic protective housing, which encloses the waterproofing and ventilating housing and thermistor protection housing.

6. The device for humidity measurement according to claim 2, further comprising:

an output circuit, adapted to receive a pulse-width modulation (PWM) signal representing an ambient humidity value outputted by the microcontroller, convert the PWM signal into a constant-current signal, and output the constant-current signal.

7. The device for humidity measurement according to claim 1, further comprising:

an output circuit, adapted to receive a pulse-width modulation (PWM) signal representing an ambient humidity value outputted by the microcontroller, convert the PWM signal into a constant-current signal, and output the constant-current signal.

8. A method for humidity measurement, comprising:

receiving, by a microcontroller, a frequency signal corresponding to a humidity-sensitive capacitor and a frequency signal corresponding to a reference capacitor outputted by the humidity-sensitive capacitor and the reference capacitor, respectively;

obtaining, by the microcontroller, frequency values representing the capacitances of the humidity-sensitive capacitor and the reference capacitor based on the frequency signals corresponding to the humidity-sensitive capacitor and the reference capacitor; and obtaining, by the microcontroller, a current ambient humidity value based on a function of $RH=K\times(Fs-F0)+A$, wherein RH denotes the current ambient humidity value, K denotes a sensitivity of a humidity measurement circuit, and A denotes an intercept of the humidity measurement circuit.

9. The method for humidity measurement according to claim 8, further comprising:

determining, by the microcontroller, whether the obtained current ambient humidity value reaches a preset ambient humidity threshold, and if so, heating the humidity-sensitive capacitor by a heating resistor, so as to form a positive difference between humidity-sensitive capacitor surface temperature and ambient temperature;

obtaining, by the microcontroller, a humidity-sensitive capacitor surface temperature and a current ambient temperature, based on a first resistance signal representing the humidity-sensitive capacitor surface temperature outputted by a first thermistor and a second resistance signal representing the current ambient temperature outputted by a second thermistor;

obtaining, by the microcontroller, a first saturated vapor pressure at the humidity-sensitive capacitor surface temperature and a second saturated vapor pressure at the current ambient temperature, based on the humidity-sensitive capacitor surface temperature and the current ambient temperature, respectively; and obtaining, by the microcontroller, an actual ambient humidity value based on a product of a humidity-sensitive capacitor surface humidity value and a ratio of the first saturated vapor pressure to the second saturated vapor pressure.

10. The method for humidity measurement according to claim 9, further comprising:

arranging a waterproofing and ventilating housing which encloses the humidity-sensitive capacitor, the first thermistor and the heating resistor.

11. The method for humidity measurement according to claim 10, further comprising:

arranging a protection housing which encloses the second thermistor.

12. The method for humidity measurement according to claim 11, further comprising:

arranging a plastic protective housing which encloses the waterproofing and ventilating housing and thermistor protection housing.

13. The method for humidity measurement according to claim 9, further comprising:

converting a pulse-width modulation (PWM) signal representing an ambient humidity value outputted by the microcontroller into a constant-current signal, and outputting the constant-current signal.

14. The method for humidity measurement according to claim 8, further comprising:

converting a pulse-width modulation (PWM) signal representing an ambient humidity value outputted by the microcontroller into a constant-current signal, and outputting the constant-current signal.

* * * * *